United States Patent
Coose et al.

(10) Patent No.: US 7,638,014 B2
(45) Date of Patent: Dec. 29, 2009

(54) METHOD OF PRODUCING A PANTS-TYPE DIAPER

(75) Inventors: Thomas R. Coose, Plymouth, WI (US); John A. McCabe, Sheboygan Falls, WI (US); Peter J. Jenquin, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 64 days.

(21) Appl. No.: 11/083,765

(22) Filed: Mar. 18, 2005

(65) Prior Publication Data

US 2005/0257881 A1    Nov. 24, 2005

Related U.S. Application Data

(60) Provisional application No. 60/573,648, filed on May 21, 2004.

(51) Int. Cl.
*B32B 38/04* (2006.01)
(52) U.S. Cl. .......... 156/250; 156/265; 156/270
(58) Field of Classification Search ......... 156/161, 156/436, 179, 265, 257, 270, 229, 260, 250
See application file for complete search history.

(56) References Cited

U.S. PATENT DOCUMENTS

| | | |
|---|---|---|
| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |

(Continued)

FOREIGN PATENT DOCUMENTS

BE    1007854    11/1995

(Continued)

OTHER PUBLICATIONS

Reciprocating Mechanisms, Ingenious Mechanisms for Designers and Inventors, Franklin Jones vol. 1

*Primary Examiner*—Philip C Tucker
*Assistant Examiner*—Sing P Chan
(74) *Attorney, Agent, or Firm*—Ryan Kromholz & Manion S.C.

(57) ABSTRACT

A method for producing disposable undergarments is disclosed. The method generally comprises combining a first layer, comprising an elastic material sandwiched between layers of nonwoven material, and a second layer, comprising a backing material and a graphically printed applied patch of material layer.

6 Claims, 5 Drawing Sheets

U.S. PATENT DOCUMENTS

| | | |
|---|---|---|
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A * | 8/1975 | Gellert et al. ............... 604/366 |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |

| Patent | Date | Inventor | Patent | Date | Inventor |
|---|---|---|---|---|---|
| 4,675,062 A | 6/1987 | Instance | 5,486,253 A | 1/1996 | Otruba |
| 4,693,056 A | 9/1987 | Raszewski | 5,494,622 A | 2/1996 | Heath et al. |
| 4,701,239 A | 10/1987 | Craig | 5,531,850 A | 7/1996 | Herrmann |
| 4,726,874 A | 2/1988 | VanVliet | 5,540,647 A | 7/1996 | Weiermann et al. |
| 4,726,876 A | 2/1988 | Tomsovic et al. | 5,545,275 A | 8/1996 | Herrin et al. |
| 4,743,241 A | 5/1988 | Igaue et al. | 5,545,285 A | 8/1996 | Johnson |
| 4,751,997 A | 6/1988 | Hirsch | 5,552,013 A | 9/1996 | Ehlert et al. |
| 4,753,429 A | 6/1988 | Irvine et al. | 5,556,360 A | 9/1996 | Kober et al. |
| 4,756,141 A | 7/1988 | Hirsch et al. | 5,556,504 A | 9/1996 | Rajala et al. |
| 4,764,325 A | 8/1988 | Angstadt | 5,560,793 A | 10/1996 | Ruscher et al. |
| 4,765,780 A | 8/1988 | Angstadt | 5,602,747 A | 2/1997 | Rajala |
| 4,776,920 A | 10/1988 | Ryan | 5,624,420 A | 4/1997 | Bridges et al. |
| 4,777,513 A | 10/1988 | Nelson | 5,624,428 A | 4/1997 | Sauer |
| 4,782,647 A | 11/1988 | Williams et al. | 5,628,738 A | 5/1997 | Suekane |
| 4,785,986 A | 11/1988 | Daane et al. | 5,634,917 A | 6/1997 | Fujioka et al. |
| 4,795,510 A | 1/1989 | Wittrock et al. | 5,643,165 A | 7/1997 | Klekamp |
| 4,801,345 A | 1/1989 | Dussaud et al. | 5,643,396 A | 7/1997 | Rajala et al. |
| 4,802,570 A | 2/1989 | Hirsch et al. | 5,645,543 A | 7/1997 | Nomura et al. |
| 4,840,609 A | 6/1989 | Jones et al. | 5,659,229 A | 8/1997 | Rajala |
| 4,845,964 A | 7/1989 | Bors et al. | 5,660,657 A | 8/1997 | Rajala et al. |
| 4,864,802 A | 9/1989 | D'Angelo | 5,660,665 A | 8/1997 | Jalonen |
| 4,880,102 A | 11/1989 | Indrebo | 5,683,376 A | 11/1997 | Kato et al. |
| 4,888,231 A | 12/1989 | Angstadt | RE35,687 E | 12/1997 | Igaue et al. |
| 4,892,536 A | 1/1990 | Des Marais et al. | 5,693,165 A | 12/1997 | Schmitz |
| 4,904,440 A | 2/1990 | Angstadt | 5,699,653 A | 12/1997 | Hartman et al. |
| 4,908,175 A | 3/1990 | Angstadt | 5,707,470 A | 1/1998 | Rajala et al. |
| 4,909,019 A | 3/1990 | Delacretaz et al. | 5,711,832 A | 1/1998 | Glaug et al. |
| 4,925,520 A | 5/1990 | Beaudoin et al. | 5,725,518 A | 3/1998 | Coates |
| 4,927,322 A | 5/1990 | Schweizer et al. | 5,745,922 A | 5/1998 | Rajala et al. |
| 4,927,582 A | 5/1990 | Bryson | 5,746,869 A | 5/1998 | Hayden et al. |
| 4,937,887 A | 7/1990 | Schreiner | 5,749,989 A | 5/1998 | Linman et al. |
| 4,963,072 A | 10/1990 | Miley et al. | 5,766,389 A * | 6/1998 | Brandon et al. ................ 156/64 |
| 4,987,940 A | 1/1991 | Straub et al. | 5,788,797 A | 8/1998 | Herrin et al. |
| 4,994,010 A | 2/1991 | Doderer-Winkler | 5,817,199 A | 10/1998 | Brennecke et al. |
| 5,000,806 A | 3/1991 | Merkatoris et al. | 5,829,164 A | 11/1998 | Kotitschke |
| 5,021,111 A | 6/1991 | Swenson | 5,836,931 A | 11/1998 | Toyoda et al. |
| 5,025,910 A | 6/1991 | Lasure et al. | 5,858,012 A | 1/1999 | Yamaki et al. |
| 5,045,039 A | 9/1991 | Bay | 5,865,393 A | 2/1999 | Kreft et al. |
| 5,062,597 A | 11/1991 | Martin et al. | 5,868,727 A | 2/1999 | Barr et al. |
| 5,064,179 A | 11/1991 | Martin | 5,876,027 A | 3/1999 | Fukui et al. |
| 5,080,741 A | 1/1992 | Nomura et al. | 5,876,792 A | 3/1999 | Caldwell |
| 5,094,658 A | 3/1992 | Smithe et al. | 5,879,500 A | 3/1999 | Herrin et al. |
| 5,096,532 A | 3/1992 | Neuwirth et al. | 5,902,431 A * | 5/1999 | Wilkinson et al. .......... 156/159 |
| 5,108,017 A | 4/1992 | Adamski, Jr. et al. | 5,932,039 A | 8/1999 | Popp et al. |
| 5,109,767 A | 5/1992 | Nyfeler et al. | 5,938,193 A | 8/1999 | Bluemle et al. |
| 5,110,403 A | 5/1992 | Ehlert | 5,964,970 A | 10/1999 | Woolwine et al. |
| 5,127,981 A | 7/1992 | Straub et al. | 6,036,805 A | 3/2000 | McNichols |
| 5,131,525 A | 7/1992 | Musschoot | 6,043,836 A | 3/2000 | Kerr et al. |
| 5,147,487 A | 9/1992 | Nomura et al. | 6,050,517 A | 4/2000 | Dobrescu et al. |
| 5,163,594 A | 11/1992 | Meyer | 6,074,110 A | 6/2000 | Verlinden et al. |
| 5,171,239 A | 12/1992 | Igaue et al. | 6,076,442 A | 6/2000 | Arterburn et al. |
| 5,176,244 A | 1/1993 | Radzins et al. | 6,098,249 A | 8/2000 | Toney et al. |
| 5,183,252 A | 2/1993 | Wolber et al. | 6,123,792 A | 9/2000 | Samida et al. |
| 5,188,627 A | 2/1993 | Igaue et al. | 6,183,576 B1 | 2/2001 | Couillard et al. |
| 5,195,684 A | 3/1993 | Radzins | 6,210,386 B1 | 4/2001 | Inoue |
| 5,203,043 A | 4/1993 | Riedel | 6,212,859 B1 | 4/2001 | Bielik, Jr. et al. |
| 5,213,645 A | 5/1993 | Nomura et al. | 6,214,147 B1 * | 4/2001 | Mortellite et al. ........... 156/201 |
| 5,223,069 A | 6/1993 | Tokuno et al. | 6,250,048 B1 | 6/2001 | Linkiewicz |
| 5,226,992 A | 7/1993 | Morman | 6,264,784 B1 | 7/2001 | Menard et al. |
| 5,246,433 A | 9/1993 | Hasse et al. | 6,276,421 B1 | 8/2001 | Valenti et al. |
| 5,267,933 A | 12/1993 | Precoma | 6,306,122 B1 | 10/2001 | Narawa et al. |
| 5,308,345 A | 5/1994 | Herrin | 6,309,336 B1 | 10/2001 | Muessig et al. |
| 5,328,438 A | 7/1994 | Crowley | 6,312,420 B1 | 11/2001 | Sasaki et al. |
| 5,340,424 A | 8/1994 | Matsushita | 6,314,333 B1 | 11/2001 | Rajala et al. |
| 5,368,893 A | 11/1994 | Sommer et al. | 6,315,022 B1 | 11/2001 | Herrin et al. |
| 5,407,513 A | 4/1995 | Hayden et al. | 6,336,921 B1 | 1/2002 | Kato et al. |
| 5,415,649 A | 5/1995 | Watanabe et al. | 6,358,350 B1 | 3/2002 | Glaug et al. |
| 5,421,924 A | 6/1995 | Ziegelhoffer et al. | 6,369,291 B1 | 4/2002 | Uchimoto et al. |
| 5,424,025 A | 6/1995 | Hanschen et al. | 6,375,769 B1 | 4/2002 | Quereshi et al. |
| 5,429,576 A | 7/1995 | Doderer-Winkler | 6,391,013 B1 | 5/2002 | Suzuki et al. |
| 5,435,802 A | 7/1995 | Kober | 6,416,697 B1 | 7/2002 | Venturino et al. |
| 5,449,353 A | 9/1995 | Watanabe et al. | 6,443,389 B1 | 9/2002 | Palone |
| 5,464,401 A | 11/1995 | Hasse et al. | 6,446,795 B1 | 9/2002 | Allen et al. |

| | | | |
|---|---|---|---|
| 6,473,669 B2 | 10/2002 | Rajala et al. | |
| 6,475,325 B1 | 11/2002 | Parrish et al. | |
| 6,478,786 B1 | 11/2002 | Gloug et al. | |
| 6,482,278 B1 | 11/2002 | McCabe et al. | |
| 6,494,244 B2 | 12/2002 | Parrish et al. | |
| 6,521,320 B2 | 2/2003 | McCabe et al. | |
| 6,524,423 B1 | 2/2003 | Hilt et al. | |
| 6,551,228 B1 | 4/2003 | Richards | |
| 6,551,430 B1 | 4/2003 | Glaug et al. | |
| 6,554,815 B1 | 4/2003 | Umebayashi | |
| 6,572,520 B2 | 6/2003 | Blumle | |
| 6,581,517 B1 | 6/2003 | Becker et al. | |
| 6,596,108 B2 | 7/2003 | McCabe | |
| 6,605,172 B1 | 8/2003 | Anderson et al. | |
| 6,605,173 B2 | 8/2003 | Glaug et al. | |
| 6,637,583 B1 | 10/2003 | Andersson | |
| 6,648,122 B1 | 11/2003 | Hirsch et al. | |
| 6,649,010 B2 | 11/2003 | Parrish et al. | |
| 6,656,309 B1 * | 12/2003 | Parker et al. | 156/249 |
| 6,659,150 B1 | 12/2003 | Perkins et al. | |
| 6,659,991 B2 | 12/2003 | Suckane | |
| 6,675,552 B2 | 1/2004 | Kunz et al. | |
| 6,684,925 B2 | 2/2004 | Nagate et al. | |
| 6,766,817 B2 | 7/2004 | da Silva | |
| D497,991 S | 11/2004 | Otsubo et al. | |
| 6,820,671 B2 | 11/2004 | Calvert | |
| 6,837,840 B2 | 1/2005 | Yonekawa et al. | |
| 6,840,616 B2 | 1/2005 | Summers | |
| 6,852,186 B1 | 2/2005 | Matsuda et al. | |
| 6,875,202 B2 | 4/2005 | Kumasaka et al. | |
| 6,893,528 B2 | 5/2005 | Middelstadt et al. | |
| 6,918,404 B2 | 7/2005 | Dias da Silva | |
| 6,978,486 B2 | 12/2005 | Zhou et al. | |
| 7,066,586 B2 | 6/2006 | da Silva | |
| 7,077,393 B2 | 7/2006 | Ishida | |
| 7,172,666 B2 | 2/2007 | Groves et al. | |
| 7,214,174 B2 | 5/2007 | Allen et al. | |
| 7,247,219 B2 | 7/2007 | O'Dowd | |
| 2001/0012813 A1 | 8/2001 | Bluemle | |
| 2001/0017181 A1 | 8/2001 | Otruba et al. | |
| 2002/0046802 A1 | 4/2002 | Tachibana et al. | |
| 2002/0059013 A1 | 5/2002 | Rajala et al. | |
| 2003/0000620 A1 | 1/2003 | Herrin et al. | |
| 2003/0015209 A1 | 1/2003 | Gingras et al. | |
| 2003/0052148 A1 | 3/2003 | Rajala et al. | |
| 2003/0066585 A1 | 4/2003 | McCabe | |
| 2003/0083638 A1 | 5/2003 | Malee | |
| 2003/0084984 A1 | 5/2003 | Glaug et al. | |
| 2003/0089447 A1 * | 5/2003 | Molee et al. | 156/161 |
| 2003/0135189 A1 | 7/2003 | Umebayashi | |
| 2004/0007328 A1 | 1/2004 | Popp et al. | |
| 2004/0016500 A1 | 1/2004 | Tachibana et al. | |
| 2004/0112517 A1 | 6/2004 | Groves et al. | |
| 2004/0164482 A1 | 8/2004 | Edinger | |
| 2005/0000628 A1 | 1/2005 | Norrley | |
| 2005/0196538 A1 | 9/2005 | Sommer et al. | |
| 2005/0230056 A1 | 10/2005 | Meyer et al. | |
| 2005/0230449 A1 | 10/2005 | Meyer et al. | |
| 2005/0233881 A1 | 10/2005 | Meyer | |
| 2005/0234412 A1 | 10/2005 | Andrews et al. | |
| 2005/0257881 A1 | 11/2005 | Coose et al. | |
| 2005/0275148 A1 | 12/2005 | Beaudoin et al. | |
| 2006/0021300 A1 | 2/2006 | Tada et al. | |
| 2006/0137298 A1 | 6/2006 | Oshita et al. | |
| 2006/0224137 A1 | 10/2006 | McCabe et al. | |
| 2006/0265867 A1 | 11/2006 | Schaap | |
| 2007/0074953 A1 | 4/2007 | McCabe | |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0206208 | 12/1986 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

* cited by examiner

METHOD OF PRODUCING A PANTS-TYPE DIAPER

RELATED APPLICATION

This application claims the benefit of U.S. Provisional Patent Application Ser. No. 60/573,648, filed 21 May 2004, and entitled "Method of Producing a Pants-Type Diaper."

BACKGROUND OF THE INVENTION

The present invention relates to disposable undergarments and, more specifically, to methods and apparatuses for forming disposable undergarments.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

One such method to produce a disposable undergarment is shown in Umebayashi, U.S. Appl. No. 2003/013518. The application discloses a process of producing a disposable undergarment wherein a layer of elastic material is adhered between two nonwoven layers. Further along the assembly process, a reinforcing material is added to the layers, followed by an absorbent pad, and then a backing layer is added to the above combined layers. While this process will produce a disposable undergarment, it has been observed that there may potentially be more efficient ways of producing the disposable undergarments.

SUMMARY OF THE INVENTION

The present invention provides for a method and apparatus for producing disposable undergarments. Compared to previous designs and processes, the present invention results in less material use, less material waste, higher line speeds and higher efficiencies due to an improved overall process.

The process provides a single roll of nonwoven material, which is slit into two equal segments. The segments are then routed and guided so that they overlap one another, with a layer of elastic material also being fed between the two segments. The nonwoven segments and the elastic strands are then pressed together. The resulting web laminate will be slit again, providing two separate elasticized nonwoven laminates that will be combined with an outer nonwoven material to form a complete chassis web assembly.

An outer nonwoven backing material and one or two optional graphic applique panels are combined and pressed together at a separate station along the assembly line. A separate backing/applique panel web assembly will be combined with each of the nonwoven/elastic layers. The two separate nonwoven/elastic layers and the backing/applique panel layers are then pressed and adhesively joined together to form a chassis web for disposable undergarments. The web may have absorbent pads (typically contained within an insert or core) or other decorative material added along the process. The resulting undergarments are formed from a process that uses less material and is more efficient than previous methods.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Figure 1:
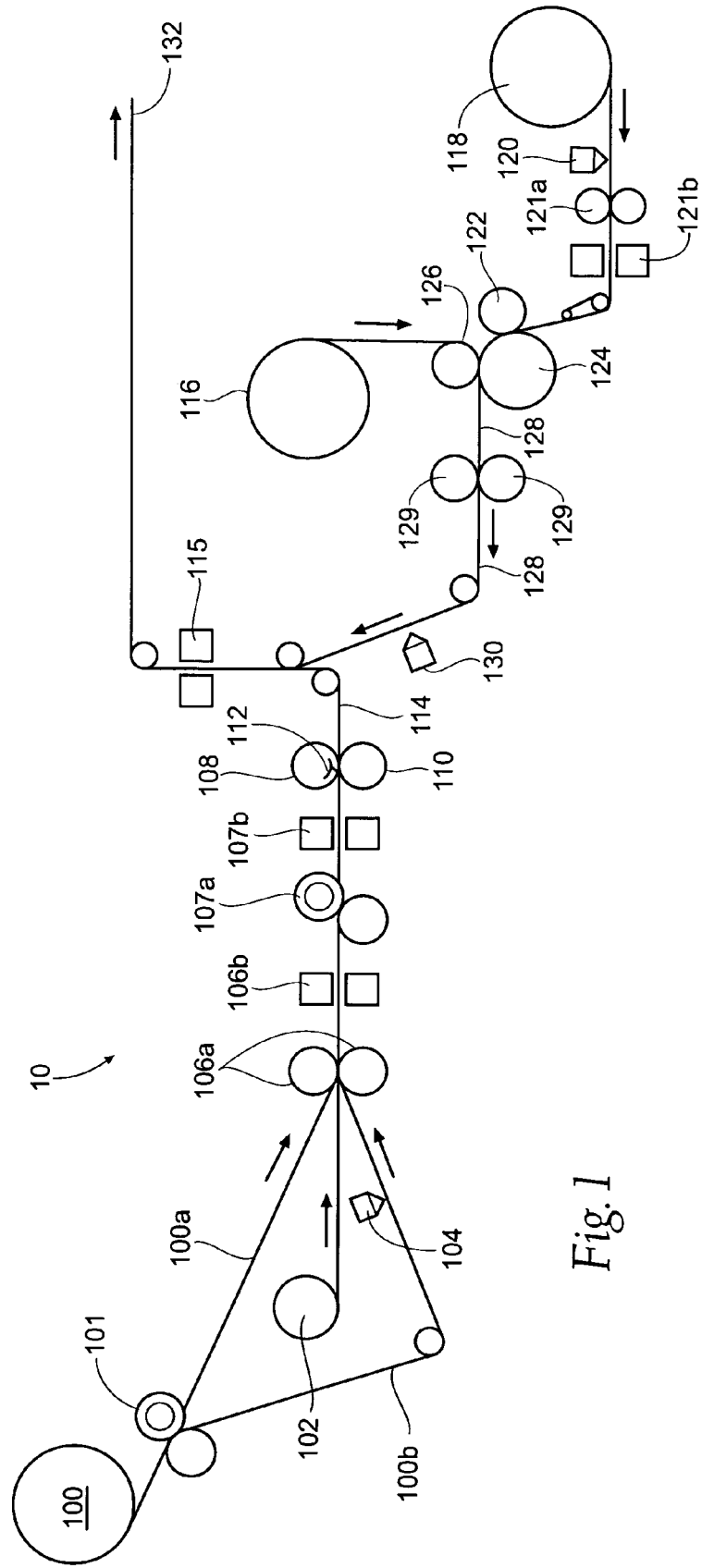
FIG. 1 is a diagrammatic illustration of a method of producing undergarments according to the present invention.

FIG. 1 shows a diagrammatic illustration of an embodiment of the present invention. A system 10 for producing the chassis assembly for disposable undergarments is shown. FIG. 1 shows two segments or layers of nonwoven material 100a and 100b, slit by slitter 101 from a common roll 100, preferably having equal widths, fed into the system 10. A roll or layer or strands of elastic material 102 are also fed into the system 10, with the elastic material 102 being fed intermediate of the two nonwoven layers of material 100a and 100b. An adhesive applicator 104 applies an adhesive coating to one of the layers of nonwoven material 100a or 100b. Alternatively, the adhesive coating may be applied to both nonwoven layers 100a and 100b, or to the elastic material 102. The design of the nonwoven materials 100a and 100b and the elastic material 102 should determine where and how the adhesive applicator applies an adhesive to the system 10, and any arrangement should not be considered a limiting factor. The adhesive applicator 104 may supply a hot melt adhesive or any other suitable adhesive that will sufficiently adhere the elastic material 102 to the layers of nonwoven material 100a and 100b. The nonwoven layers 100a and 100b and the elastic material 102 are then fed through a pair of pressing rollers 106a to securely bind the elastic material 102 to the nonwoven layers 100a and 100b. The nonwoven layers 100a and 100b and the elastic material 102 are next fed through an edge folder 106b. After being pressed together and having the edges folded, the layers 100a, 100b, and 102 are then fed through a slitting station 107a and a spreader assembly 107b to position these separate elasticized web laminates on new process lines. These newly centered webs are then each fed through a cutting roller 108 and an anvil roller 110. The anvil roller 110 supplies resistance for the cutting roller 108, which has cutting means 112 located on its exterior surface. The cutting means 112 cuts through one layer of the nonwoven layers 100a or 100b and severs the elastic material 102 positioned between the nonwoven layers 100a and 100b. The cutting means 112 may cut both nonwoven layers 100a and 100b, but it is preferable that only layer 100a is severed. Layer 100a refers only to the layer near the cutting means 112 and should not be limited to any spatial orientation. A resultant web of material 114 is formed having predetermined individual areas with and without elastic material on or elastic forces in the web 114.

Still referring to FIG. 1, a second feed area is located on the right side of the schematic. A web of backing material 116 is fed into the system 10. Also, a web of graphically printed material 118 is fed into the system 10. An adhesive applicator 120, similar to the adhesive applicator 104, will apply an adhesive material to the graphically printed material 118. The graphically printed material 118 will proceed through a slitting station 121a and a web spreader assembly 121b before encountering a cutting roll 122 and a pressing or transfer roll 124. The pressing/transfer roll 124, along with another transferring roll 126, will transfer the graphically printed material 118 onto the backing material 116. Further along the process, a pair of pressing rolls 129 will assist in binding the backing material 116 and the graphically printed material 118 together, resulting in a second web of material 128. Provided the backing material 116 and the graphically printed material 118 are adequately secured to one another after passing the transferring roll 126, the pressing rolls 129 may not be necessary in the system. It should be noted that the graphically printed material 118 can be slit and separated prior to or after the adhesive applicator 120 so that ultimately graphics can appear on both front and back of the finished pants type diaper.

Figure 1B:
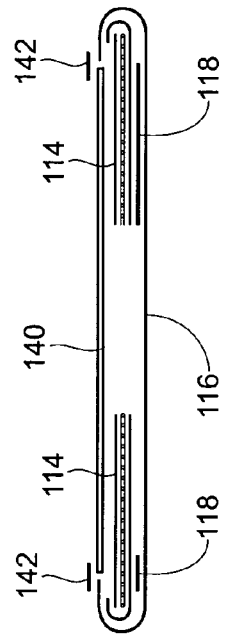
FIG. 1B is a cross-sectional view of the resulting web further including an insert or core and cover strips.
Figure 1A:
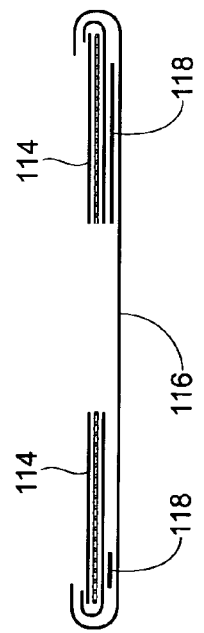
FIG. 1A is a cross-sectional view of the resulting web.

A third adhesive applicator 130, similar to the previously mentioned adhesive applicators 120 and 104, applies an adhesive to the second web of material 128 after the graphically printed material and the backing material have been combined. The second web of material 128 and the resultant webs of material 114 are then pressed together and the edges are folded at second edge folder 115, forming a final web 132 that comprises all of the previous layers. The final web 132 as shown in FIG. 1A will proceed for further modifications, such as adding decorative material, absorbent material, or cutting of leg holes, if not previously added, folding, sealing and severing the web 132 into individual undergarments. As shown in FIG. 1B, the final web may have an insert or core 140 placed between the inwardly folded edges of the nonwoven material 100. In addition, one or more cover strips 142 may be adhered to conceal the junction of the edges and the insert.

Figure 2:
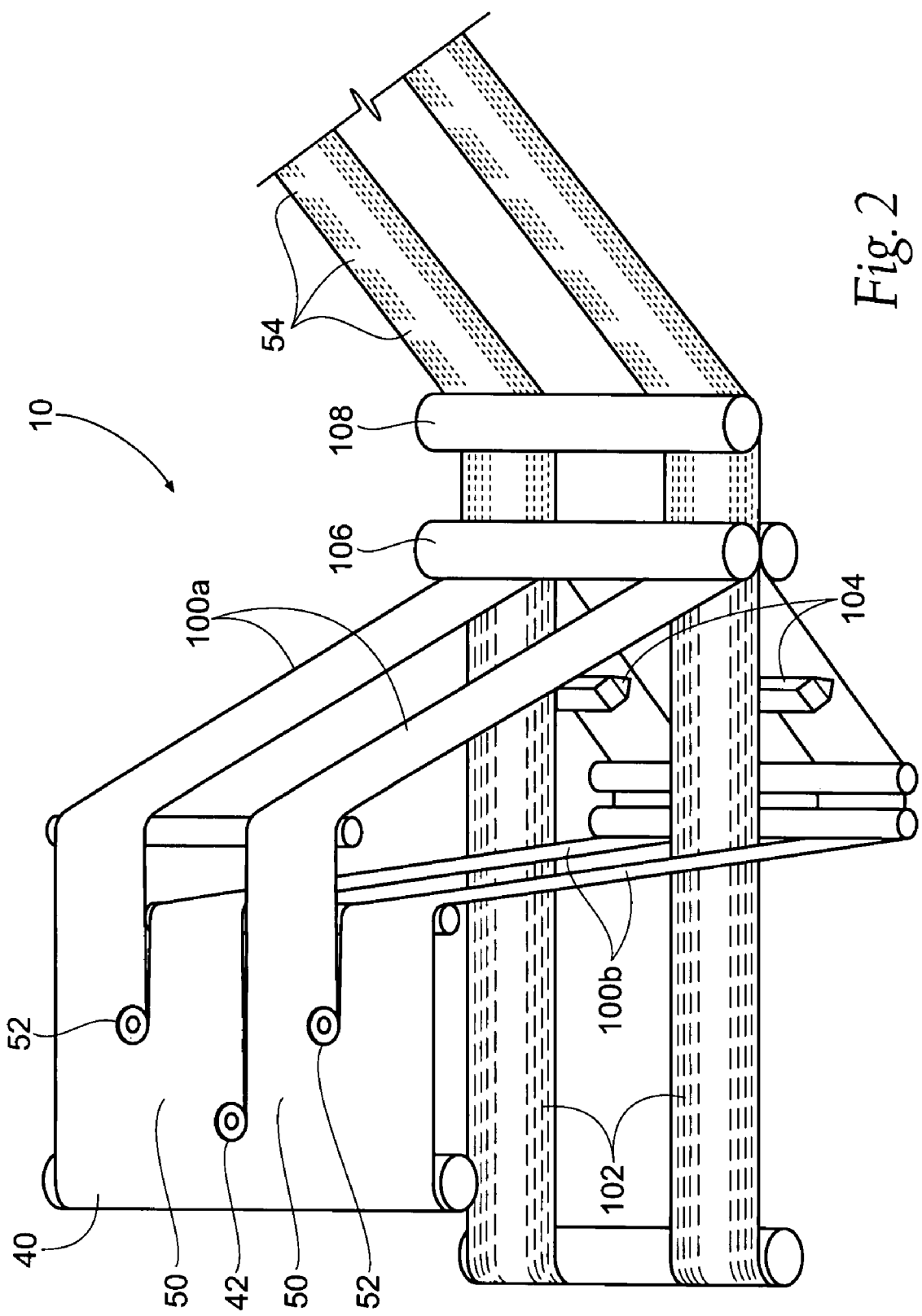
FIG. 2 is a schematic representation of a section of an alternate assembly process according to the present invention.

FIG. 2 is an alternate schematic representation of the introductory feed area of the present system. A single preliminary layer of nonwoven material 40 provides a starting point for the system 10. The preliminary layer 40 proceeds towards a first slitting device 42, which will cut the preliminary layer 40 into a pair of feeder layers 50. The feeder layers 50 each form the basis of an eventual final web 132 (see FIGS. 1A and 4). As previously stated, the preliminary layer 40 provides for two systems 10 shown in FIG. 1, as understood in the present invention to run concurrently. The feeder layer 50 proceeds towards a second slitting device 52, which will cut and slit the feeder layer 50 into the nonwoven layers 100a and 100b, preferably with the nonwoven layers 100a and 100b having equal widths. The four nonwoven layers, two layers 100a and two layers 100b, are separated and fed into the system 10 on opposing sides of the two elastic layers 102, with a nonwoven layer 100a and 100b supplied for each elastic layer 102. As shown the adhesive applicator 104 applies an adhesive to one of the nonwoven layers 100 that results from each of the feeder layers 50 after being slit by the second slitting device 52. However, it is possible the adhesive applicator 104 may provide adhesive prior to the layers proceeding to the pressing roller 106.

Still referring to FIG. 2, the pressing roller 106 and the cutting roller 108 are shown to be sufficiently wide enough so that single rollers may be used to process all of the layers. While this is preferred for efficiency and cost purposes, it is possible to have individual rollers for each set of combined layers and still fall within the scope of the present invention.

Figure 3:
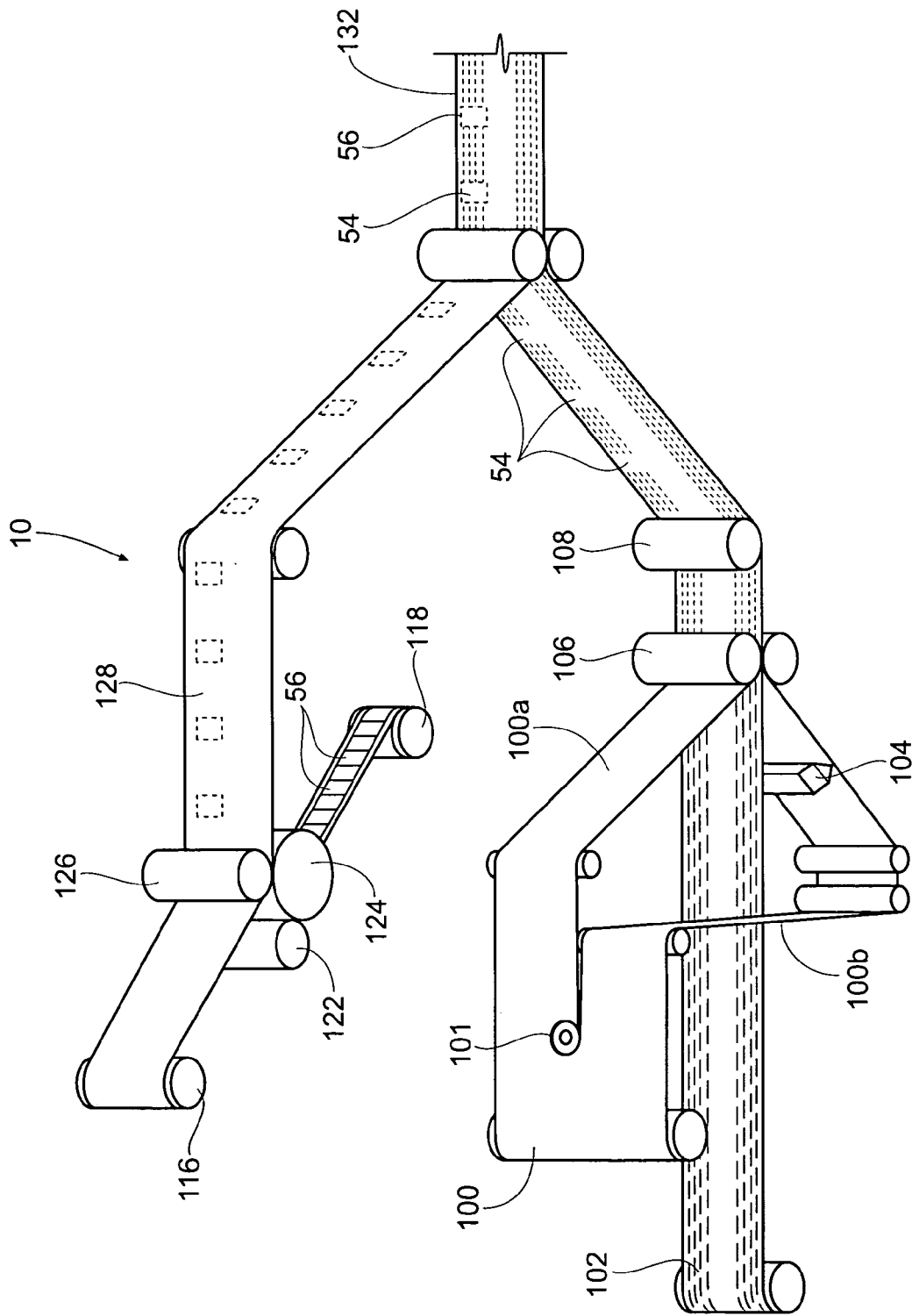
FIG. 3 is a schematic view of a method and apparatus that may be used to produce undergarments in accordance with the present invention.

FIG. 3 provides a further schematic representation of a full width chassis assembly fabrication system 10 similar to that shown in FIG. 1. Like elements are denoted by like reference numerals. The nonwoven layers 100a and 100b originate from the single feeder layer of material 100. The feeder layer 100 proceeds towards the second slitting device 101, which will cut and slit the feeder layer 100 into the nonwoven layers 100a and 100b, preferably with the nonwoven layers 100a and 100b having equal widths, which are then separated and fed into the system 10 on opposing sides of the elastic layer 102. The elastic layer 102 is a stretched sheet, which may be made up of threads, scrims, elastic sheets, or other elastic materials that will provide elastic properties for the undergarments. An adhesive material is applied to the nonwoven layers 100a and 100b and the elastic layer 102, as previously described in FIG. 1. Likewise, as discussed with respect to FIG. 2, adhesive material may be applied to anywhere before the layers 100a, 100b, and 102 encounter the pressing roll 106. The layers 100a, 100b, and 102 are fed through the pressing rolls 106. Each respective web is then fed through each cutting roller 108. The cutting roller 108 is not necessarily limited to devices that cut the elastic material 102, but also may include die presses, ultrasonic methods, or heated presses that will remove the elastic material 102 (or the elastic forces) from a specific predetermined area 54 on the nonwoven layers 100.

Still referring to FIG. 3, the backing material 116 and the graphically printed material 118 are shown being fed together through the transfer roll 124 and the pressing roll 126. As previously noted with respect to FIG. 1, the web of graphically printed material 118 passes the cutting roll 122. The cutting roll 122 will cut the graphically printed material into specific graphically printed sections 56 of predetermined area. The web of graphically printed material 118 is preferably fed into the system at a slower rate than that of the backing material 116, for instance by controlling the speed of the feed roll for material 118. A slower feed rate allows the graphically printed sections 56 to be cut to a shorter length and spaced apart from one another in a distance that will correspond to one graphically printed section per an individual undergarment. Each of the resulting graphically enhanced sections 56 will be approximately the same size as that of the area 54 having the elastic material 102 removed. Preferably, the graphically enhanced sections 56 will be slightly larger than the areas 54, to insure that the graphically enhanced section adequately covers the elastic force free area 54. The second web of material 128 exiting the transfer roll 124 and the press roll 126 displays such an arrangement. The final web of material 132 includes the graphically enhanced sections 56 aligned with the areas where the elastic material 102 was removed. It should again be noted that the graphically printed material 118 can be slit and separated prior to or after hot melt application so that graphics can appear on both front and back of the finished pants-type diaper.

Figure 4:
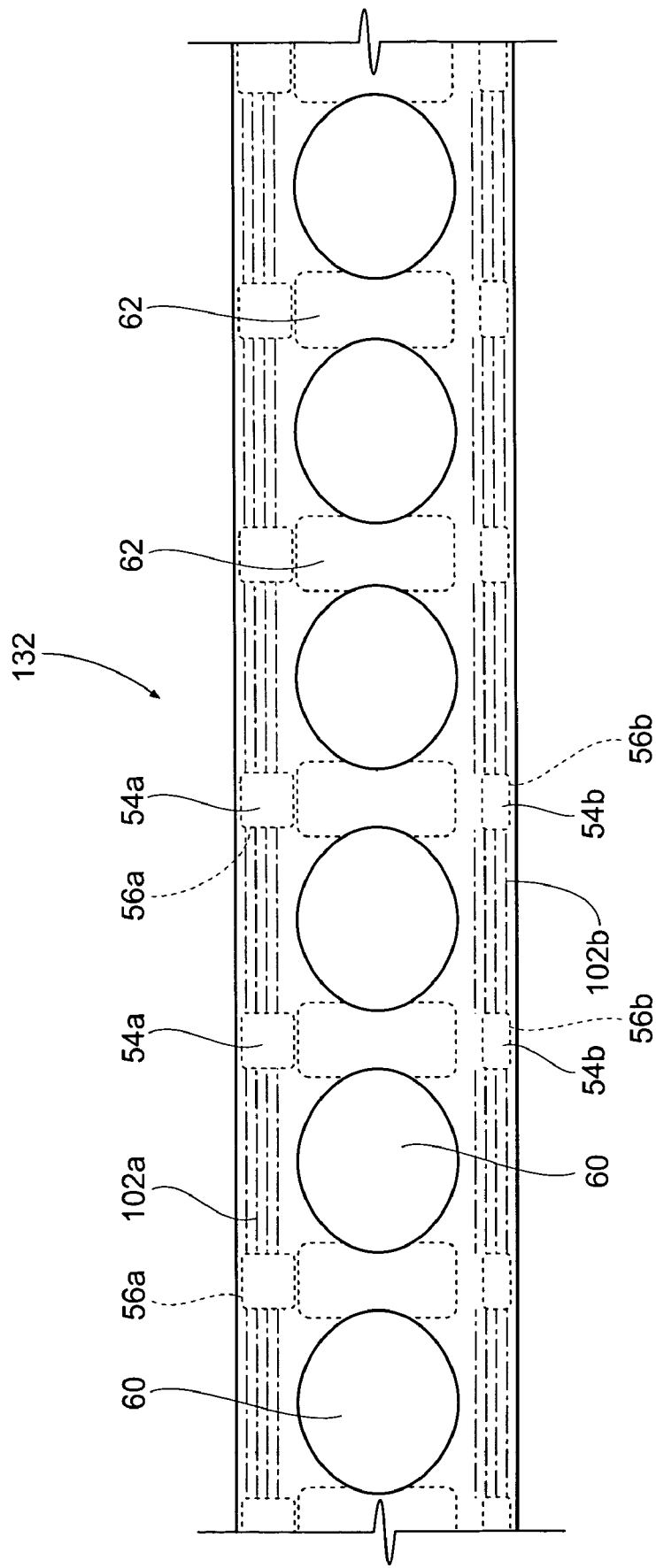
FIG. 4 is a top planar view of a resultant layer formed according to the present invention.

The final web of material 132 can be viewed in FIG. 4. As shown, the final web 132 has leg holes 60 cut from the final web 132 and, also, an absorbent layer of material 62 added to the final web 132. It is understood that the leg holes 60 and the absorbent layer 62 may be added at varying positions during the undergarment formation process. The graphically enhanced sections 56a correspond to the areas 54a, which are located where the elastic layers 102a are positioned on the final web 132. FIG. 4 shows the elastic layers 102b as non-continuous elements that are interrupted by additional non-adhered areas 54b and the graphically enhanced sections 56b. It will be understood that non-adhered sections 54b and graphically enhanced sections 56b could be omitted on the elastic layers 102b and still fall within the scope of the present invention. It will also be understood that the final web 132 may be designed without the elastic layer 102b present.

Figure 5:
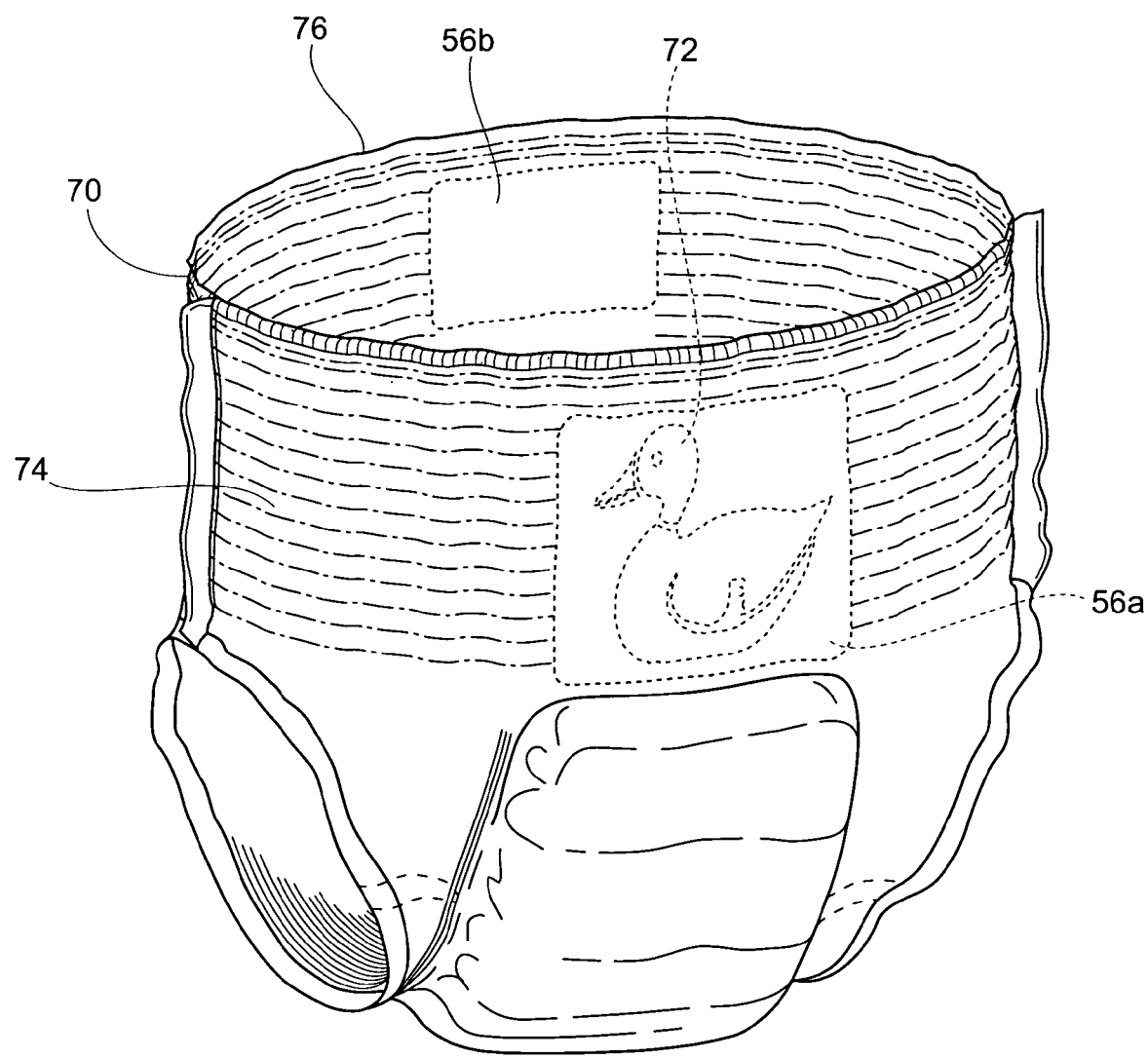
FIG. 5 is a finished disposable undergarment produced according to the present invention.

A single resultant undergarment 70 is shown in FIG. 5. The undergarment 70 has the graphically enhanced sections 56a and 56b displayed. A decorative design 72 may appear on the graphically enhanced section 56a. The undergarment is shown with a graphically enhanced section 56a located on a front side 74 of the undergarment 70 and a second section 56b located on the opposite side 76 of the undergarment 70. If desired, only one graphically enhanced section may be formed in each undergarment 70. In the case of two graphically enhanced sections 56a and 56b, the system would operate as previously shown and described with respect to the previous figures, except that the graphically printed web of material 118 would be divided into separate strips, or possibly two webs of material 118 would be fed into the system. Likewise, when the elastic material 102 passes the cutting roller 108, the cutting roller 108 would remove a second section of elastic material 102 that would correspond to the backside 76 of the undergarment 70.

The method described and shown has advantages over prior art designs. Providing a layer consisting of nonwoven material and elastic material separate from a layer consisting of the backing material and the graphically enhanced material provides for a system that improves overall process control as compared to prior-art designs. Generally, the process adheres together two separate layers to form a portion of the final garment web. Prior designs have a first layer, with every subsequent layer of material adhered separately to the first layer. Thus, each time a new layer is added, such as the backing material or the graphically enhanced material, another possible chance for misalignment or nonadherance arises. The present method minimizes the potential for such errors, which also leads to higher line speeds and material savings.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of making an undergarment, the method comprising the steps of:
    a. providing an elastic sheet material and first and second oppositely disposed layers of nonwoven fabric material;
    b. adhering said elastic material to said facing sides of said first and second layers of nonwoven fabric material;
    c. severing a pre-selected portion of said elastic material;
    d. providing a discontinuous section of graphically printed material, said section having a predetermined area exceeding the area of said severed portion of said elastic material;
    e. providing a sheet of backing material;
    f. adhering said graphically printed material to one side of said sheet of backing material;
    g. after step (f), merging and adhering said backing material and said graphically printed material to said second nonwoven layer of fabric material wherein said graphically printed material is aligned with and extending over said severed portion of said elastic material;
    h. folding said backing material over a portion of said first layer of nonwoven fabric thereby forming an assembled chassis web; and
    i. prior to step (g), folding a portion of said second layer of nonwoven fabric over a portion of said first layer on nonwoven fabric.

2. The method according to claim 1 further including the step of adhering an absorbent pad to said assembled chassis web.

3. The method according to claim 1 further including the steps of:
    providing a feeder layer of nonwoven material; and
    slitting said feeder layer of nonwoven material to form said first and second layers of nonwoven material.

4. A method of making an undergarment, the method comprising the steps of:
    a. providing an elastic sheet material and first and second oppositely disposed layers of nonwoven fabric material;
    b. adhering a first portion of said elastic material to said facing sides of said first and second layers of nonwoven fabric material to define a second non-adhering portion of said elastic sheet material;
    c. severing said second portion of said elastic material from said first portion of said elastic material;
    d. providing a discontinuous section of graphically printed material, said section having a predetermined area exceeding the area of said second non-adhering portion of said elastic material;
    e. providing a sheet of backing material;
    f. adhering said graphically printed material to one side of said sheet of backing material;
    g. after step (f), merging and adhering said backing material and said graphically printed material to said second nonwoven layer of fabric material wherein said graphically printed material is aligned with and extending over said non-adhering portion of said elastic material;
    h. folding said backing material over a portion of said first layer of nonwoven fabric thereby forming an assembled chassis web; and
    i. prior to step (g), folding a portion of said second layer of nonwoven fabric over a portion of said first layer of nonwoven fabric.

5. The method according to claim 4 further including the step of adhering an absorbent pad to said assembled chassis web.

6. The method according to claim 4 further including the steps of:
    providing a feeder layer of nonwoven material; and
    slitting said feeder layer of nonwoven material to form said first and second layers of nonwoven material.

* * * * *